United States Patent
Huang et al.

(10) Patent No.: US 6,500,879 B1
(45) Date of Patent: *Dec. 31, 2002

(54) DENTAL COMPOSITION AND METHOD

(75) Inventors: Chin-Teh Huang, Dover, DE (US); Kewang Lu, Dover, DE (US); Mingxin Fan, Dover, DE (US); Paul Hammesfahr, Wyoming, DE (US)

(73) Assignee: Dentsply Research & Development Corp.

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/259,833

(22) Filed: Jun. 15, 1994

Related U.S. Application Data

(63) Continuation-in-part of application No. 08/049,221, filed on Apr. 19, 1993, now Pat. No. 5,338,773.

(51) Int. Cl.$^7$ ............................................. A61K 6/083
(52) U.S. Cl. ...................... 523/116; 523/118; 524/436; 524/437; 526/318.1
(58) Field of Search ............................. 523/116, 118; 524/436, 437; 562/432, 467; 526/318.1

(56) References Cited

U.S. PATENT DOCUMENTS

| | | |
|---|---|---|
| 2,549,732 A | 4/1951 | Weaver |
| 2,568,331 A | 9/1951 | Frilette ............... 260/40 |
| 2,628,209 A | 2/1953 | Fisk ................... 260/40 |
| 2,673,151 A | 3/1954 | Gerhart ............... 95/7 |
| 3,013,895 A | 12/1961 | Agruss ................ 117/38 |
| 3,234,181 A | 2/1966 | Olivier ................ 260/47 |
| 3,407,176 A | 10/1968 | Lonerini .............. 260/47 |
| 3,421,501 A | 1/1969 | Beightol ............... 128/90 |
| 3,422,061 A | 1/1969 | Gall ................... 260/47 |
| 3,424,718 A | 1/1969 | Angelo ................. 260/47 |
| 3,448,089 A | 6/1969 | Celeste ................ 260/78.5 |
| 3,518,762 A | 7/1970 | Takeuchi ............... 32/15 |
| 3,655,605 A | 4/1972 | Smith .................. 260/29.6 |
| 3,814,717 A | 6/1974 | Wilson et al. .......... 260/29.6 |
| 3,855,379 A | 12/1974 | Araki et al. ........... 260/77.5 |
| 3,954,475 A | 5/1976 | Abonham et al. ......... 96/67 |
| 3,959,350 A | 5/1976 | Rogers ................. 260/47 |
| 4,001,939 A | 1/1977 | Gross .................. 32/15 |
| 4,012,840 A | 3/1977 | Takeuchi et al. ........ 32/15 |
| 4,016,124 A | 4/1977 | Crisp et al. ........... 260/29.6 |
| 4,021,915 A | 5/1977 | Rubens ................. 32/15 |
| 4,035,327 A | 7/1977 | Shahidi et al. ......... 260/22 |
| 4,043,327 A | 8/1977 | Potter et al. .......... 128/89 R |
| 4,064,629 A | 12/1977 | Stoner et al. .......... 32/15 |
| 4,079,516 A | 3/1978 | Marshall ............... 32/40 |
| 4,089,830 A | 5/1978 | Tezu ................... 260/29.6 |
| 4,143,018 A | 3/1979 | Crisp et al. ........... 260/29.6 |
| 4,180,911 A | 1/1980 | Bullock ................ 433/9 |
| 4,209,434 A | 6/1980 | Wilson et al. .......... 260/29.6 |
| 4,212,970 A | 7/1980 | Iwasaki ................ 542/455 |
| 4,243,567 A | 1/1981 | Potter ................. 260/29.6 |
| 4,304,893 A | 12/1981 | Orlowski ............... 526/309 |
| 4,306,651 A | 12/1981 | Muhlbauer .............. 206/219 |
| 4,317,681 A | 3/1982 | Beede et al. ........... 106/85 |
| 4,322,207 A | 3/1982 | Madsen ................. 433/216 |
| 4,324,591 A | 4/1982 | Beede et al. ........... 106/85 |
| 4,336,175 A | 6/1982 | Gibbs .................. 524/726 |
| 4,340,532 A | 7/1982 | Lee, Jr. et al. ........ 524/854 |
| 4,342,677 A | 8/1982 | Muramatsu .............. 523/116 |
| 4,358,549 A | 11/1982 | Randklev ............... 523/117 |
| 4,360,605 A | 11/1982 | Schmitt et al. ......... 523/116 |
| 4,372,836 A | 2/1983 | Schmitt et al. ......... 204/159.23 |
| 4,374,936 A | 2/1983 | Tomioka et al. ......... 523/116 |
| 4,376,835 A | 3/1983 | Schmitt et al. ......... 523/116 |
| 4,378,213 A | 3/1983 | Severy ................. 433/213 |
| 4,396,117 A | 8/1983 | Muhlbauer .............. 106/219 |
| 4,401,773 A | 8/1983 | Smyth .................. 523/116 |
| 4,457,818 A | 7/1984 | Denyer et al. .......... 204/159.19 |
| 4,459,193 A | 7/1984 | Ratcliffe et al. ....... 204/159.23 |
| 4,468,251 A | 8/1984 | Hausselt et al. ........ 106/1.18 |
| 4,492,777 A | 1/1985 | Denton, Jr. et al. ..... 523/115 |
| 4,512,340 A | 4/1985 | Buck ................... 128/90 |
| 4,514,527 A | 4/1985 | Bowen .................. 523/155 |
| 4,515,267 A | 5/1985 | Welsh .................. 206/219 |
| 4,521,267 A | 6/1985 | Bowen .................. 523/116 |
| 4,521,550 A | 6/1985 | Bowen .................. 523/116 |
| 4,525,256 A | 6/1985 | Martin ................. 204/159.18 |
| 4,529,384 A | 7/1985 | Severy ................. 433/213 |
| 4,539,382 A | 9/1985 | Omura et al. ........... 526/276 |
| 4,544,359 A | 10/1985 | Waknine ................ 523/115 |
| 4,547,531 A | 10/1985 | Waknine ................ 523/116 |
| 4,588,756 A | 5/1986 | Bowen .................. 523/116 |
| 4,602,076 A | 7/1986 | Ratcliffe et al. ....... 522/7 |
| 4,612,361 A | 9/1986 | Peters ................. 528/185 |
| 4,629,746 A | 12/1986 | Michl et al. ........... 523/117 |
| 4,648,532 A | 3/1987 | Green .................. 222/82 |

(List continued on next page.)

FOREIGN PATENT DOCUMENTS

| | | |
|---|---|---|
| CA | 934085 | 9/1973 |
| CA | 968741 | 6/1975 |
| CA | 969299 | 6/1975 |

(List continued on next page.)

OTHER PUBLICATIONS

McKinney et al, Wear and Microhardening of Two Experimental Dental Composites, Journal of Dental Research, vol. 65, p. 848, Abstract No. 1101 (1986).

(List continued on next page.)

Primary Examiner—Peter Szekely
(74) Attorney, Agent, or Firm—Dale R. Lovercheck; James B. Bieber

(57) ABSTRACT

The invention provides dental cement compositions and methods of using them for binding hard tooth material, metal and ceramic. The cement compositions include shelf stable complexes of ethylenically unsaturated monomers reacted with cations. The cements have superior adhesion to tooth without separately acid etching dentin or enamel. Compositions of are useful as dental luting cements, liners, pit and fissure seal bases and restoratives.

39 Claims, No Drawings

U.S. PATENT DOCUMENTS

| | | | |
|---|---|---|---|
| 4,657,941 A | 4/1987 | Blackwell et al. | 522/14 |
| 4,659,384 A | 4/1987 | Daigo et al. | 106/35 |
| 4,659,751 A | 4/1987 | Bowen | 523/116 |
| 4,664,629 A | 5/1987 | Chodkawski | 433/228.1 |
| 4,680,373 A | 7/1987 | Gallagher et al. | 528/185 |
| 4,705,836 A | 11/1987 | Ohtsuka et al. | 526/318.1 |
| 4,713,403 A | 12/1987 | Yoshida et al. | 523/115 |
| 4,719,149 A | 1/1988 | Aasen et al. | 428/473 |
| 4,732,943 A | 3/1988 | Beech et al. | 525/303 |
| 4,746,686 A | 5/1988 | Waller | 522/14 |
| 4,755,620 A | 7/1988 | Iwamoto et al. | 560/224 |
| 4,758,612 A | 7/1988 | Wilson | 524/5 |
| 4,794,157 A | 12/1988 | Berdahl et al. | 528/208 |
| 4,797,431 A | 1/1989 | Billington et al. | 523/116 |
| 4,806,381 A | 2/1989 | Engelbecht et al. | 427/2 |
| 4,813,876 A | 3/1989 | Wang | 433/224 |
| 4,814,362 A | 3/1989 | Billington et al. | 523/117 |
| 4,816,495 A | 3/1989 | Blackwell et al. | 522/14 |
| 4,839,401 A | 6/1989 | Waknine | 522/14 |
| 4,861,808 A | 8/1989 | Billington et al. | 523/16 |
| 4,864,015 A | 9/1989 | Calla et al. | 528/352 |
| 4,867,817 A | 9/1989 | Kneafsey et al. | |
| 4,872,936 A | 10/1989 | Engelbrecth | 156/307.3 |
| 4,880,660 A | 11/1989 | Aasen et al. | 427/2 |
| 4,918,136 A | 4/1990 | Kawaguchi et al. | 524/751 |
| 4,964,911 A | 10/1990 | Ibsen et al. | 106/35 |
| 4,966,934 A | 10/1990 | Huang et al. | 524/315 |
| 4,985,198 A | 1/1991 | Hirasawa et al. | 560/130 |
| 5,028,638 A | 7/1991 | Heid et al. | 522/14 |
| 5,034,433 A | 7/1991 | Cohen et al. | 523/400 |
| 5,035,615 A | 7/1991 | Din | 433/39 |
| 5,051,453 A | 9/1991 | Okabayashi et al. | 523/116 |
| 5,055,497 A | 10/1991 | Okada et al. | 523/116 |
| 5,063,257 A | 11/1991 | Akahane et al. | 523/116 |
| 5,079,277 A | 1/1992 | Wilson et al. | 523/116 |
| 5,084,491 A | 1/1992 | Kerby | 523/116 |
| 5,130,347 A | 7/1992 | Mitra | 523/149 |
| 5,154,613 A | 10/1992 | Cohen | 433/228.1 |
| 5,154,762 A | 10/1992 | Mitra et al. | 106/35 |
| 5,171,763 A | 12/1992 | Ohno et al. | 523/116 |
| 5,179,135 A | 1/1993 | Ellis et al. | 523/116 |
| 5,189,077 A | 2/1993 | Kerby | 523/116 |
| 5,218,070 A * | 6/1993 | Blackwell | 526/318.1 |
| 5,227,413 A * | 7/1993 | Mitra | 523/116 |
| 5,234,972 A | 8/1993 | Saitoh et al. | 523/118 |
| 5,270,351 A | 12/1993 | Bowen | 523/116 |
| 5,276,068 A | 1/1994 | Waknine | 522/28 |
| 5,318,999 A | 6/1994 | Mitra et al. | 522/57 |
| 5,321,053 A | 6/1994 | Hino et al. | 522/26 |
| 5,338,773 A | 8/1994 | Lu et al. | 523/116 |
| 5,340,850 A | 8/1994 | Shimasue | 523/115 |
| 5,354,785 A | 10/1994 | Rheinberger et al. | 523/116 |
| 5,401,783 A | 3/1995 | Bowen | 523/116 |
| 5,427,613 A | 6/1995 | Arnold | 106/35 |

FOREIGN PATENT DOCUMENTS

| | | |
|---|---|---|
| CA | 983190 | 2/1976 |
| CA | 1018294 | 9/1977 |
| CA | 1020687 | 11/1977 |
| CA | 1028441 | 3/1978 |
| CA | 1117242 | 1/1982 |
| CA | 1131388 | 9/1982 |
| CA | 1136796 | 11/1982 |
| CA | 1154895 | 10/1983 |
| CA | 1159984 | 1/1984 |
| CA | 1164124 | 3/1984 |
| CA | 1176787 | 10/1984 |
| CA | 1179094 | 12/1984 |
| CA | 1194637 | 10/1985 |
| CA | 1198847 | 12/1985 |
| CA | 1200647 | 2/1986 |
| CA | 1213699 | 11/1986 |
| CA | 1216982 | 1/1987 |
| CA | 1243796 | 10/1988 |
| CA | 1244177 | 11/1988 |
| CA | 1259149 | 9/1989 |
| CA | 1261992 | 9/1989 |
| CA | 1262791 | 11/1989 |
| CA | 1262981 | 11/1989 |
| CA | 1269790 | 5/1990 |
| CA | 2009471 | 8/1990 |
| CA | 2011438 | 10/1990 |
| CA | 2038695 | 9/1991 |
| CA | 2051333 | 3/1992 |
| EP | 0 241 277 A2 | 10/1987 |
| EP | 0 244 959 | 11/1987 |
| EP | 0 325 038 A3 | 7/1989 |
| EP | 0 335 645 A3 | 10/1989 |
| EP | 0 470 446 A1 | 2/1992 |
| GB | 2 000 789 A | 1/1979 |
| GB | 2 156 347 A | 10/1985 |
| GB | 2 202 221 A | 9/1988 |
| WO | PCT 80/00409 | 3/1980 |
| WO | 88/05651 | 8/1988 |
| WO | 93/12757 | 7/1993 |
| WO | 93/12758 | 7/1993 |
| WO | WO 93/12759 | 7/1993 |
| WO | 93/12760 | 7/1993 |
| WO | 93/14039 | 7/1993 |

OTHER PUBLICATIONS

Antonucci et al, Formulation and Evaluation of ResinModified Glass Ionomer Cements, Transactions Thirteenth Annual Meeting of the Society for Biomaterials, Jun. 3–7, 1987, vol. X.

Antonucci, Toughened Glass–Ionomer Cements, Trends & Techniques, Apr. 1988, vol. 5, No. 3.

Antonucci et al, Polymer–Modified Glass Ionomer Cements, Journal Dental Research, vol. 68, p. 251, Abstract #555 (1989).

Rusz et al, Adhesive Properties of Polymer—and Resin—MOdified Glass Ionomer Cements, Journal of Dental Research, vol. 69, p. 366, Abstract #2058 (1990).

Rusz et al, Adhesive Properties of Modified Glass–Ionomer Cements, Dental Materials, Jan. 1992, Adhesive properties of modified glass–ionomer cements.

Erickson et al, Evaluation of Experimental Fluoride–Containing Restorative Materials, Journal of Dental Research vol. 66, Special Edition, Mar. 11–15, 1987.

Wilson et al, Glass–Ionomer Cement, p. 51.

Prosser et al, Litho–ionomer Cements and their Technological Applications, J. Chem. Tech. Biotechnol 1979, 29, 69–87.

Wilson et al, Developments in Ionic Polymers–1, 1983, pp. 217–267.

McGinniss, Radiation Curing, vol. 19, pp. 607–624.

Swartz et al, Long Term F. Release from Glass Ionomer Cements, Journal of Dental Research, Feb. 1984/vol. 63/No. 2.

Erickson et al, Evaluation of Experimental Fluoride–Containing Restorative Material, 65th General Session, IADR, Mar. 11–15, 1987, Abstract No. 1114.

Mathis et al, Properties of A New Glass Ionomer/Composite Resin Hybrid Restorative, Abstract No. 51.

Heilmann et al, Chemistry of Alkenyl Azlactones. I. Radiation–Sensitive Materials Derived from Azlactone–Containing Copolymers, Journal of Polymer Science: Polymer Chemistry Edition, vol. 22 1179–1186 (1984).

* cited by examiner

DENTAL COMPOSITION AND METHOD

This is a continuation-in-part of U.S. patent application Ser. No. 08/049,221 filed Apr. 19, 1993 now U.S. Pat. No. 5,338,773.

The invention relates to dental compositions and methods of use thereof to bind hard tooth, metal and ceramic. The invention provides compositions including complexes formed by reacting multivalent cation with acid moieties of ethylenically unsaturated Monomers and prepolymers. The invention provides compositions with superior adhesion to dentin, enamel and cementum without the need for separate steps of acid etching dental enamel to adhere thereto. Compositions of the invention are useful as dental luting cements, liners, bases and restoratives. The compositions of the invention are hydrolytically stable. The heterogeneous multi-phase dental compositions of the invention show improved mechanical strength, for example, improved bond strength to tooth and are less sensitive to the effects of moisture.

Glass ionomers are described by A. Wilson in U.S. Pat. Nos. 5,079,277 and 4,758,612. Prior art glass ionomer compositions are combinations of a polyalkenoic acid polymer such as polyacrylic acid and an elutable glass which provides a source of cations to react with the polyacrylic acid. Prior art glass ionomers are brittle and weak in high stress applications and set poorly in the presence of moisture unless protected from water. Prior art pit and fissure materials include polymerizable hydrophobic resins with essentially no adhesion to tooth. They are adhered by infiltrating micromechanical undercuts produced by acid etching. They harden in-situ to protect the tooth from colonization by bacteria in order to reduce caries, but because they are difficult to use they are not universally employed to achieve this valuable result. They require the tooth be cleaned, acid etched, washed, dried and isolated by rubber dam to maintain dryness, to avoid contamination by saliva, and achieve suitable results. The procedure is thus uncomfortable for the patient and laborious for the dentist. The present invention provides pit and fissure sealant compositions which are applied to tooth without a separate acid etching step.

Olivier in U.S. Pat. No. 3,234,181 discloses melt-fabricable end-capped aromatic polyimides.

Lonerini in U.S. Pat. No. 3,407,176 discloses polyamide-acids and polymide from a mixture of dianhydrides.

Gall in U.S. Pat. No. 3,422,061 discloses coalesceable polyimide powders from a polycarboxylic aromatic dianhydride and phenylene diamine.

Angelo in U.S. Pat. No. 3,424,718 discloses copolymers of aromatic tetracarboxylic acids with at least two organic diamines.

Rogers in U.S. Pat. No. 3,959,350 discloses melt-fusible linear polyimide of 2,2-bis(3,4-dicarboxyphenyl)-hexafluoropropane dianhydride.

Madsen in U.S. Pat. No. 4,322,207 discloses dental cleaning slurry.

Beede et al in U.S. Pat. No. 4,324,591 discloses modifying agents for ion-leachable cement compositions.

Gibbs in U.S. Pat. No. 4,336,175 discloses polymide precursor solutions.

Schmitt et al in U.S. Pat. No. 4,372,836 disclose light curable acrylic dental composition with calcium fluoride pigment.

Smyth in U.S. Pat. No. 4,401,773 discloses highly reactive ion-leachable glass.

Denyer et al in U.S. Pat. No. 4,457,818 discloses dental compositions from urethane acrylate, diacrylate monomer, camphorquinone and dimethylaminoethyl methacrylate.

Ratcliffe et al in U.S. Pat. No. 4,459,193 discloses dental compositions containing camphorquinone and organic peroxide as catalyst.

Denton, Jr. et al in U.S. Pat. No. 4,492,777 discloses heat treated barium or strontium glass.

Bowen in U.S. Pat. No. 4,514,527 discloses method for obtaining strong adhesive bonding of composites to dentin enamel and other substrates.

Bowen in U.S. Pat. No. 4,521,550 discloses method for obtaining strong adhesive bonding of composites to dentin, enamel and other substrates.

Martin in U.S. Pat. No. 4,525,256 discloses photopolymerizable composition including catalyst comprising diketone plus 4-(N,N-Dimethylamino)benzoic acid or ester thereof.

Bowen in U.S. Pat. No. 4,588,756 discloses multi-step method for obtaining strong adhesive bonding of composites to dentin, enamel and other substrates.

Ratcliffe et al in U.S. Pat. No. 4,602,076 discloses photopolymerizable compositions.

Peters in U.S. Pat. No. 4,612,361 discloses poly (etherimides) and compositions containing the same.

Blackwell et al in U.S. Pat. No. 4,657,941 discloses biologically compatible adhesive containing a phosphorus adhesion promoter and a sulfinic accelerator.

Bowen in U.S. Pat. No. 4,659,751 discloses simplified method for obtained strong adhesive bonding of composites to dentin, enamel and other substrates.

Gallagher et al in U.S. Pat. No. 4,680,373 discloses process for the production of a random copolymer containing repeating polyimide units and repeating polyetherimide units.

Aasen et al in U.S. Pat. No. 4,719,149 discloses method for priming hard tissue.

Berdahl et al in U.S. Pat. No. 4,794,157 discloses polyetherimide copolymers, and method for making.

Engelbrecht et al in U.S. Pat. No. 4,806,381 discloses polymerizable compounds containing acid and acid derivatives, mixtures containing the same, and use thereof.

Blackwell et al in U.S. Pat. No. 4,816,495 discloses biologically compatible adhesive visible light curable compositions.

Calla et al in U.S. Pat. No. 4,864,015 discloses method for making thianthrene dianhydride and polyimides obtained therefrom.

Engelbrecht in U.S. Pat. No. 4,872,936 teaches dental cement mixtures containing polymerizable unsaturated monomers and/or oligomers and/or prepolymers containing acid groups and/or their reactive acid-derivative groups.

Aasen et al in U.S. Pat. No. 4,880,660 discloses method for priming hard tissue.

Kawaguchi et al in U.S. Pat. No. 4,918,136 discloses adhesive composition.

Ibsen et al in U.S. Pat. No. 4,964,911 discloses adhesive bonding of acrylic resins, especially in dentistry.

Huang et al in U.S. Pat. No. 4,966,934 discloses biological compatible adhesive containing a phosphorous adhesion promoter and accelerator.

Hirasawa et al in U.S. Pat. No. 4,985,198 discloses tooth-adhesive compounds.

Okada et al in U.S. Pat. No. 5,055,497 discloses curable resinous composition.

Akahane et al in U.S. Pat. No. 5,063,257 discloses dental glass ionomer cement compositions.

Wilson et al in U.S. Pat. No. 5,079,277 discloses polyvinylphosphonic acid and metal oxide or cermet or glass ionomer cement.

Mitra in U.S. Pat. No. 5,130,347 discloses photocurable ionomer cement systems.

Mitra et al in U.S. Pat. No. 5,154,762 discloses universal water-based medical and dental cement.

Ohno et al in U.S. Pat. No. 5,171,763 discloses curable composition.

Rambosek in Canadian Patent 873,935 discloses lithium aluminum silicate, polymer dental filling compositions.

Rossi in Canadian Patent 934,085 discloses dental restorative material of improved polishability.

Spoor in Canadian Patent 968,741 discloses production of coatings by curing with ionizing radiation.

Knight in Canadian Patent 969,299 discloses resins prepared from vinyl-ended polyurethane prepolymers.

Wailer in Canadian Patent 983,190 discloses photopolymerizable acrylic dental products.

Lee et al in Canadian Patent 1,018,294 discloses dental filling package.

O'Sullivan in Canadian Patent 1,020,687 discloses ureathaneacrylate dental filling composition.

Rockett et al in Canadian Patent 1,028,441 discloses three package dental restoration system.

Lorenz in Canadian Patent 1,117,242 discloses coating composition comprising N-vinyl-2-Pyrrolidone and an oligomer.

Osborn in Canadian Patent 1,131,388 discloses radiation curable urethane compositions.

Davies et al in Canadian Patent 1,136,796 discloses potopolymerizable compositions.

Skudelny et al in Canadian Patent 1,154,895 discloses flowable mixture and use of synthetic calcium silicate.

Schaefer in Canadian Patent 1,159,984 discloses dental material having a plastics material base.

Munk in Canadian Patent 1,164,124 discloses pourable solid mixture.

Chevreux et al in Canadian Patent 1,176,787 discloses photosetting adhesive composition.

Gruber et al in Canadian Patent 1,179,094 discloses radiation curable coating composition comprising an oligomer and a copolymerizable ultra-violet absorber.

Morgan in Canadian Patent 1,194,637 discloses UV and thermally curable, thermoplastic-containing compositions.

Ratcliffe et al in Canadian Patent 1,198,847 discloses dental Compositions.

Szycher et al in Canadian Patent 1,200,647 discloses actinic radiation cured polyurethane acrylic copolymer.

Temin et al in Canadian Patent 1,213,699 discloses dental restorative composition.

Moran in Canadian Patent 1,216,982 discloses cure to elastomers composition

Ibsen et al in Canadian Patent 1,243,796 discloses dental composite and porcelain repair.

Ibsen in Canadian Patent 1,244,177 discloses methacrylate functional resin dental composite and porcelain repair compositions.

Ying in Canadian Patent 1,259,149 discloses dental restorative composition containing monofunctional monomer.

Randklev in Canadian Patent 1,261,992 discloses orthodontic bracket adhesive compositions.

Waknine in Canadian Patent 1,262,791 discloses a two component (Paste-Paste) self curing dental restorative.

Dougherty et al in Canadian Patent 1,262,981 discloses methods for posterior dental restoration employing light curable packable compositions.

Waknine in Canadian Patent 1,269,790 discloses dental restorative material.

Heid et al in Canadian Patent Application 2,009,471 discloses Hybrid plastic filling material.

Ibsen et al in Canadian Patent Application 2,011,438 discloses light-curable ionomer dental cement.

Rheinberger et al in Canadian Patent Application 2,038,695 discloses polymerizable dental materials.

Rheinberger et al in Canadian Patent Application 2,051,333 discloses polymerizable dental material.

Billington in European Patent Application 0 241 277 discloses glasses and poly(carboxylic acid) cement compositions containing them.

Billington in European Patent Application 0 244 959 discloses glass/poly(carboxylic acid) cement compositions.

Montgomery in European Patent Application 0 325 038 discloses surface priming composition for proteinaceous substrates, method of making and using same.

Kawaguchi et al in European Patent Application 0 335 645 discloses adhesive composition.

Griffin et al in European Patent Application 0 470 446 A1 discloses High glass transition temperature mixed polyimides and composites formed therefrom.

Masuhara in U.K. Patent Application 2 000 789 A discloses curable composition.

Hirasawa in U.K. Patent Application 2 156 347 a discloses (Meth) acrylic acid ester compounds boundable to tooth substrates.

Akahane et al U.K. Patent Application 2 202 221 discloses glass powders for dental glass ionomer cements.

U.S. Pat. No. 4,588,756 relates to aromatic based compositions employed in dentistry as a component in a dental adhesive system requiring multiple pretreatment steps including application of an acid.

Engelbrecht in U.S. Pat. No. 4,872,936 broadly teaches dental cement mixtures containing polymerizable unsaturated monomers and/or oligomers and/or prepolymers containing acid groups and/or their reactive acid-derivative groups.

Mitra in U.S. Pat. No. 5,130,347 discloses a photocurable ionomer cement having a photocurable amid monomer.

Mitra in U.S. Pat. No. 5,154,762 discloses water soluble reducing and oxidizing agents.

It is an object of the invention is to provide new dental compositions useful as filling materials, cavity liners and bases, cements, and pit and fissure sealants other restorative materials which are adhesive to tooth structure.

It is an object of the invention to provide a composition which reduces the steps and time required to adhere metal or ceramic to tooth structure.

It is an object of the invention to provide an adhesive composition for adhesion between tooth structure and/or bone and polymeric composites.

It is an object of the invention to provide dental compositions that are relatively inexpensive and easy to manufacture.

"Monomer" as used herein means monomer or oligomer.

"Set" as used herein means a polymerizable composition undergoes a change so that it becomes firm, stiff and nonpliable.

As used herein "The MAX Lite" means THE MAX™, a curing unit for light-polymerizable dental materials sold by Dentsply International Inc. through its L. D. Caulk Division.

Throughout this disclosure unless otherwise specified amounts of each component of a composition are in percent by weight.

BRIEF DESCRIPTION OF THE INVENTION

The invention provides dental compositions and methods of using them for adhering to hard tooth structures, metal and ceramic. The compositions include shelf stable complexes of ethylenically unsaturated monomers reacted with cations. These compositions have superior adhesion to tooth without separately acid etching dentin or enamel. Compositions of the invention are useful as dental luting cements, liners, bases and restoratives pit and fissue sealants. In accordance with a method of polymerization of the invention is provided the sequence of steps of forming a substantially pliable polymerizable composition, including polymerizable complex coated particles within the scope of the general formula:

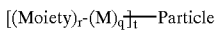
[(Moiety)$_r$-(M)$_q$]$_t$—Particle wherein each Moiety independently is a moiety having at least one acid group and at least one polymerizable group each M is a multivalent cation of Particle which forms a complex by bonding to one or more Moiety, and t, r and q each independently is a number having an average value of 1 or more, storing the polymerizable composition for at least 12 hours, and applying the polymerizable composition to a tooth.

DETAILED DESCRIPTION OF THE INVENTION

Compositions of the invention provide superior adhesion to dentin, enamel and bone. In a preferred embodiment compositions of this invention are used without a separate step of etching the surfaces to be joined. The adhesive dental materials provided by this invention include restorative materials especially cavity bases and liners, luting cements, pit and fissure sealants and filling materials.

In accordance with the invention is provided a method of polymerizing polymerizable composition which includes a polymerizable salt (complex) within the scope of the general formula (A1) and/or a novel material within the scope of general formula (A1'):

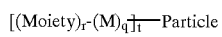
[(Moiety)$_r$-(M)$_q$]$_t$—Particle    (A1')

wherein each Moiety independently is a moiety having at least one acid group and at least one polymerizable group, each M is a multivalent cation which forms a complex by bonding to one or more Moieties; Particle is a particle, r, t, and q each individually is a number having an average value of 1 or more. In general formula A1' M is a cation of Particle. Preferably, the Particle is glass or ionomeric polymer. The composition is stable and adapted to not set in order of increasing preference for at least 12 hours, 24 hours, or 36 hours, more preferably for at least 7 days and most preferably for at least 1 year in the absence of polymerization initiation. The letter is preferably greater than 100, more preferably greater than 1,000 and most preferably greater than 10,000. A composition in accordance with a preferred embodiment of the invention includes a substantial portion of polymerizable salt within the scope of general formula A1 in equilibrium with polymerizable acid(s) and a source of multivalent cation(s). The polymerizable salt in such compositions is preferably formed by mixing a polymerizable acid and a source of multivalent cations in the presence of water. The polymerizable salt is preferably in equilibrium with the polymerizable acid and a source of multivalent cations for extended periods of time, for example, more than one year. These compositions do not require hermetic sealing to prevent substantial setting as is required by prior art compositions. Thus, these compositions advantageously form, for example, one component compositions which do not substantially set, and are thus, shelf stable preferably for more than one year. It is preferred that the salt forms on the outer surface, perferably as a coating on glass particles used as multivalent cation sources, and that upon polymerization of the polymerizable group a stronger material is formed than in prior art compositions which are multicomponent systems and/or do not include water as a component of the composition applied to a tooth. Preferably these compositions are mixed with Monomers and/or prepolymers and applied to a tooth. These compositions preferably include at least one Monomer and/or polymers which does not include an acid moiety.

More specifically the invention provides a polymerizable composition which includes a polymerizable salt (complex) within the scope of the general formula (B1) and/or a novel material within the scope of the general formula (B1'):

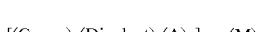
[(Group)$_o$(Divalent)$_s$(A)$_p$]$_r$—(M)$_q$    (B1)

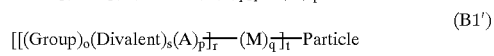
[[(Group)$_o$(Divalent)$_s$(A)$_p$]$_r$—(M)$_q$]$_t$—Particle    (B1')

wherein each Group independently is a polymerizable group, each A independently is an acid group, each Divalent independently is a divalent organic moiety, each M independently is a multivalent cation which forms a complex by bonding to one or more A; Particle is a particle and o, p, q, r, s and t each independently is a number having an average value of at least 1. Preferably M is a multivalent ion of a glass particle. This composition is adapted to not set for at least 24 hours in the absence of polymerization initiation.

Preferably polymerizable compositions in accordance with the invention include at least 1 percent by weight, more preferably at least 3 precent by weight of polymerizable complexes within the scope of general formula (A1).

Complexes within the scope of general formulas, A1 and B1, preferably have molecular weights less than 100,000; more preferably less than 20,000 and most preferably less than 5,000 and especially preferred are such complexes having molecular weights less than 1,000.

Particulate material within the scope of general formulas A1' and B1' preferably have a particle size having a longest dimension in order of increasing preference of: less than 1 mm, less than 0.1 mm, less than 0.01 mm or less than 0.001 mm.

Dental compositions of the invention include polymerizable unsaturated substituted aromatic complexes within the scope of the general formula (I):

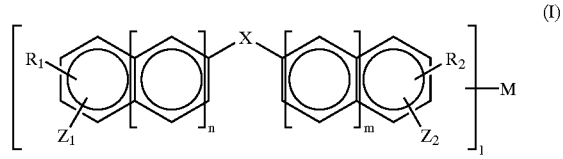

wherein X is

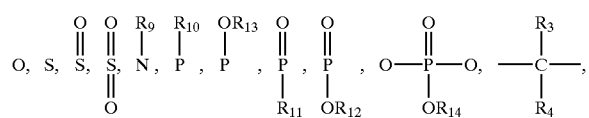

-continued
or

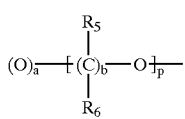

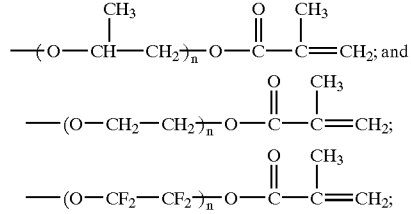

wherein $R_1$ and $R_2$ each independently is a polymerizable unsaturated moiety having from 2 to 13 carbon atoms, $R_3$, $R_4$, $R_5$, and $R_6$ each independently is hydrogen, halogen, alkyl having from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $Z_1$ and $Z_2$ each independently is a moiety including an acid group, a, m and n each independently is 0 or 1, b, and p independently is an integer from 1 to 10, l is from 1 to 3, and M is a multivalent cation which reacts with acid moieties to form a complex.

In accordance with a preferred embodiment of the invention $R_1$ and $R_2$ each independently is:

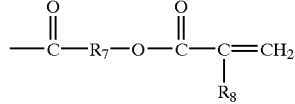

wherein $R_7$ a divalent carbon containing radical and $R_8$ is hydrogen, halogen or alkyl having from 1 to 10 carbon atoms.

In a preferred embodiment of the invention compounds are provided within the scope of general formula I wherein n and m are zero, X is oxygen, sulfonyl or ditrifluoromethyl; and $R_1$ and $R_2$ are

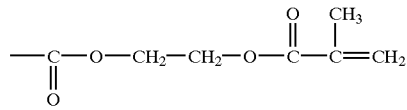

Most preferably compounds within the scope of general formula I are those wherein X is oxygen or ditrifluoromethyl, and M is barium, calcium, strontium or aluminium. Preferred polymerizable unsaturated groups $R_1$ and $R_2$ independently are alkenyl, alkenoxy, cycloalkenyl, arylalkenyl, and alkenaryl moieties; with vinyl, and styryle moieties being more preferred, and acryl and methacryl moieties that constitute the polymerizable groups of many monomers in dental materials being especially preferred.

Exemplary $R_1$ and $R_2$(meth)acrylate moieties include:

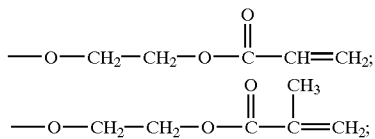

where n preferably is an integer from 1 to 10. Preferably $R_1$ and $R_2$ are (meth)acryloyloxyethyl moieties.

Preferred compounds for use in complexes within the scope of formula I include diesters which are the adducts of 2,2-bis(3,4-dicarboxylphenyl)hexafluoropropane anhydride, 4,4'-oxydiphthalic anhydride, 4,4'-sulfonyldiphthalic anhydride, respectively with 2-hydroxyethyl methacrylate. In a preferred embodiment at least two aromatic rings of a compound for use in complexes with the scope of formula I are joined through at least one saturated carbon, oxygen or sulfonyl.

Aromatic dianhydrides preferred for making compounds for use in complexes within the scope of general formula I react to form partial esters and carboxylic acid functionality. Dianhydrides having at least two aromatic rings are more preferred. Most preferably at least two aromatic rings are joined as shown in formula I to provide disruption of conjugation between the aromatic rings. It has been found that such compositions are less sensitive to light induced changes in color, and are therefore preferred when esthetic considerations are of importance. Most preferred examples are 4,4'-oxydiphthalic anhydride and 2,2-bis(3,4-dicarboxyphenyl)hexafluoropropane dianhydride.

Dental compositions in accordance with a preferred embodiment of the invention include an acid functional polymerizable organic ester for use in complexes within the scope of general formula I, water, cation elutable glass filler, and a polymerization catalyst system. Optionally, additional polymerizable monomers and/or prepolymers are included.

A composition in accordance with a preferred embodiment of the invention provides polymerizable monomer having at least one acid radical or reactive acid derivative, and a source of cations reactive with the acid moiety, and a catalyst system. Preferably the catalyst system promotes free radical polymerization and preferably includes visible light curing and/or a redox catalyst system. Preferably the composition includes liquid diluents, and/or filler adjuvants. Diluent preferably co-polymerizes with the polymerizable monomer within the scope of general formula A1. Alternatively the diluent is nonreactive with the polymerizable monomer. Water or low boiling alcohols such as methanol, ethanol, and isopropanol are nonreactive diluents. Suitable polymerizable co-monomers are disclosed in U.S. Pat. No. 4,657,941 particularly at column 3 line 5 through column 5 line 59 and U.S. Pat. No. 4,514,342 both of which are incorporated herein by reference. The filler adjuvants are preferably reactive, for example by providing a source of cations which are reactive with the acid moiety of the polymerizable monomer. Nonreactive filler is preferably included in compositions in accordance with a preferred embodiment of the invention. Optionally, fillers have surface treatments to improve compatibility and strength of the resulting composition. Exemplary fillers include silica, silicates, alumina, aluminates, calcium fluoride, strontium fluoride, glasses including fluorine glasses, ceramics and minerals including mica, zeolites, ceramics, calcium apatites and organic polymers and those disclosed in U.S. Pat. Nos. 4,758,612 and 5,079,277.

A preferred composition of the invention includes a monomer compound for use in complexes within the scope of general formula A1, at least one finely divided reactive filler which provides a source of cations reactive with the acids or acid derivative of the monomer compound and curing agent. A dental composition in accordance with the invention includes a compound for use in complexes of general formula A1, catalysts, initiators, accelerators, filler, adjuvants, source of cations, water, and diluent. Dental cements and dental filling compositions in accordance with a preferred embodiment of the invention include monomer compounds for use in complexes within the scope of general formula A1.

The compounds for use in complexes within the scope of general formula A1 have at least two different functional substituent groups, one of which is capable of addition polymerization and the other of which is carboxyl or other acid or reactive acid derivative. Most preferably these compounds include at least one polymerizable group and one or more acid or reactive acid derivative groups. Preferred compounds within the scope of general formula A1 are derived acid formed from the reaction of 4,4'-oxydiphthalic anhydride or 2,2-bis(3,4-dicarboxylphenyl) hexafluorpropane dianhydrides with a polymerizable hydroxyl or polyhydric compound to form esters and partial esters thereof.

The new salt compounds of the invention are capable of being polymerized to form linear or crosslinked polymers which contain multiple acid groups or reactive acid derivative groups that have been reacted with cations, especially those of valence 2 or greater to form poly-salts. Because the salt compounds are monomers of relatively low molecular weight with a high density of both ethylenic unsaturation and carboxylic reactive acid derivative sites, excellent curing with superior integrity occurs. The carboxyl group itself is most preferred over other acid moieties or the reactive acid derivative ions. Especially appropriate acid moieties are all those that react with oxidic, mineral, ceramic, vitreous, or metallic fillers. Examples of these other acid moieties include:

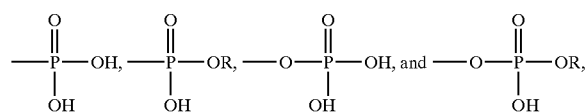

of phosphorus acids wherein R is alkyl, aryl, or vinyl; the moieties —SO$_2$H, SO$_3$H, or —O—SO$_3$H of sulfuric acids; the moieties:

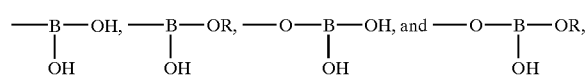

of boron acids wherein R is alkyl, aryl, or vinyl and cationic acid moieties including —NR$_2$H+ wherein R is H or alkyl. The reactive acid derivatives can be substituted with acid halides, with acid anhydrides, and with acid amides, nitrites, and esters that readily hydrolyze into acid, such as can enter into ion-exchange, neutralization, salt formation, or chelation reactions with the reactive filler. Preferred acid or reactive acid derivatives are carboxylate, phosphate, phosphonate, sulfonate, or borate acid moieties and/or of their reactive derivatives.

The compositions of the invention are formulated as one, two or more components, visible light curable, self cure, and/or dual cure product or combinations of these. The composition of a preferred embodiment of the invention includes polymerizable carboxylic acid monomer, an optional filler and/or diluent, a cationic elutable glass or other source of polyvalent cations, and a polymerization catalyst system. The polymerizable carboxylic acid monomers are chosen to provide a suitable balance of hydrophobic and hydrophilic moieties in order to provide a balanced set of properties including adhesion to metal, ceramics and tooth. They are essentially non-volatile and not critically affected by moisture during hardening within the oral cavity; and provide the ability to be used on hydrated surfaces such as found on and in teeth; and in a preferred embodiment do not require the separate steps of acid etching and adhesive priming to achieve adhesion to tooth structure.

For a better understanding of the characteristics and method of producing the preferred ethylenically unsaturated carboxylic compounds for use in complexes of the present invention the preparation of a preferred series of the compounds is carried out as follows:

In the presence of acid, base or other suitable catalyst one mole 4,4'-oxydiphthalic anhydride is reacted with two moles of a compound of the general formula R—OH, wherein R is a polymerizable unsaturated moiety having from 2 to 13 carbon atoms. This yields a liquid product which is believed to be a mixture of isomer monomers of general formulas II–IV:

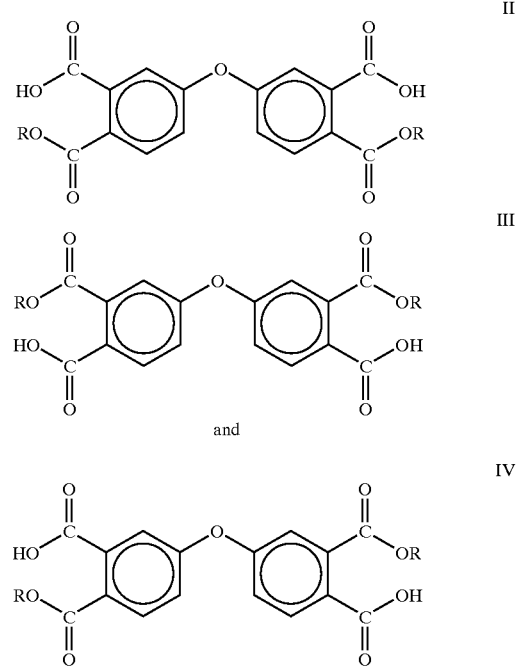

As discussed in detail in Example 3 by reacting one mole of oxydiphthalic anhydride with two moles of methacryloyloxyethyl alcohol also known as 2-hydroxyethyl methacrylate (HEMA) in the presence of catalyst a liquid product is formed which is believed to be a mixture of isomer monomers V–VII:

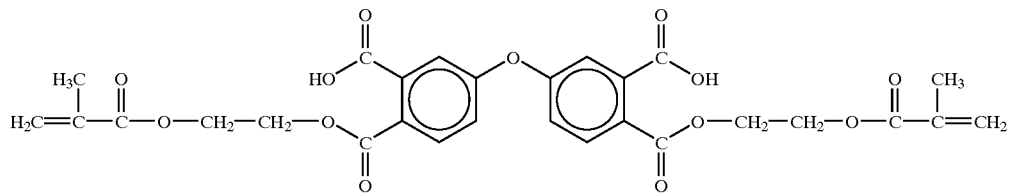

V

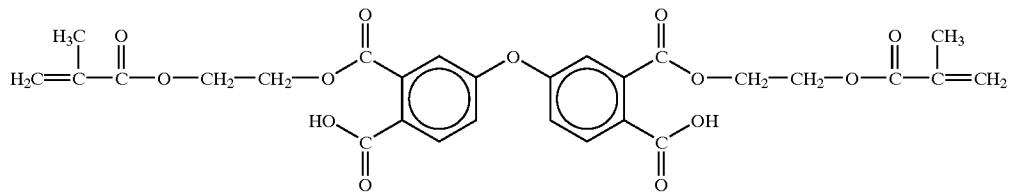

VI and

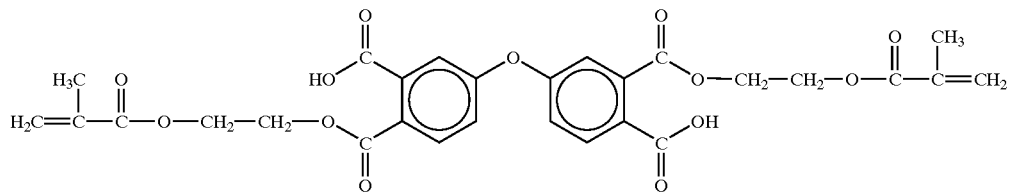

VII

Monomer compounds for use in complexes within the scope of general formula I are reactive esters which have at least one unreacted carboxylic acid group and one polymerizable group in the monomer. The number of reacted or unreacted carboxylic acid groups in the monomer is controlled by varying the reaction conditions and molar ratio of reactants. The monomer compounds of the invention polymerize by addition polymerization through the ethylenically unsaturated group. Curing agents, catalysts, initiators and/or accelerators, are used to expedite and control the polymerization. A peroxide initiator, for example benzoyl peroxide, and/or heat are useful to initiate the reaction. Accelerators enhance the reaction so that it may proceed more expeditiously at room temperature. Accelerators preferably include reducing agents such as amines or sulfinates, and/or transition metal ions. Ultraviolet and/or visible light are used with initiators and accelerators to initiate and accelerate the polymerization. Visible light curing is preferred for curing the compositions of the invention in the mouth. For preformed objects, or those cured outside the body, other forms of radiation, for example ultraviolet ionizing radiation is preferred for curing the compositions of the invention.

In accordance with the method of the invention in-vivo polymerization does not harm the patient within whom polymerization of monomer compound (or complexes) within the scope of general formula I occurs. Preferably a single part composition is induced to polymerize by the application of heat or light. To initiate by irradiation with ultraviolet or visible light the initiator, for example a benzophenone or camphorquinone is preferably used to form a single, premixed, ready to use shelf-stable composition. A preferred embodiment of the composition of the invention includes a polymerization catalyst system having a light sensitive polymerization initiator such as camphorquinone, a reducing agent such as ethyl 4-dimethylaminobenzoate (EDAB) and an oxidizing agent such as benzoyl peroxide. Redox polymerization systems known to the art are preferably used to polymerize the composition of the invention. Preferred redox polymerization catalyst systems for use in accordance with the invention include, a peroxide and tributyl boron and/or a transition metal salt. Redox polymerization catalysts and catalyst systems are those disclosed in U.S. Pat. No. 4,657,941 at column 7 line 10 through column 8 line 27 incorporated herein by reference. A particular polymerization method and system may be preferred depending on the application requirements of the material. Whatever the mode of polymerization, or "set or cure" of the composition including the salt monomers, an important characteristic of the polymers which form is that they have been prereacted with di- or polyvalent cations. The salt compounds and compositions of the invention exhibit adhesion between the resin and a cation containing surface, metal, metal oxide, tooth, and/or bone against which they are polymerized.

Fillers which are especially suited for use in compositions of the invention are inorganic glasses such as are used in glass ionomer cements. Exemplary of such fillers are those of U.S. Pat. No. 4,814,362 which is incorporated herein by reference in its entirety. Preferred fillers are glasses formed from or including, barium, calcium, strontium, lanthanum, tantalum, and/or tungsten silicates and aluminates and/or aluminosilicates, silica, including submicron silica, quartz, and/or ceramics for example, calcium hydroxy apatite. In a preferred embodiment of the invention reactive cations, especially those of calcium, strontium and aluminum, and anions especially fluoride ions; are eluted from the fillers. The fillers used in the invention preferably are reduced in particle size and in a preferred embodiment are silanated before they are incorporated into such compositions. Preferred levels of filler are from about 20% to about 85% based on the total weight of the cement composition, with from about 40% to about 85% being more preferable and about 50–80% being most preferred. If a more finely particulated filler is used, amounts of filler may be decreased due to the relative increase in surface area which attends the smaller sizes of particles. Preferred particle size distributions are from 0.02 to 50 microns, more preferably 0.1 to 10 microns, and most preferably 1 to 6 microns.

In a preferred embodiment of the invention the cations of the salts are di- and polyvalent cations, such as Sr, Ca, Al and Ba. In another preferred embodiment compositions of the invention include solvents, plasticizers, pigments, antimicrobials and therapeutics which may be time released from the composition, and oxidation inhibitors such as butylated hydroxytoluene. In addition to compounds within the scope of general formula I compositions in accordance with the invention preferably include polymerizable unsaturated diluent monomers, oligomers and/or prepolymers that do not contain any acid groups and/or salts thereof and/or reactive readily hydrolyzing acid-derivative groups thereof. One such preferred monomer is hydroxyalkyl methacrylates. Compositions of the invention may also preferably include compounds having acid groups and/or their salts and/or their readily reactive hydrolyzing derivative groups but do not contain any groups that are unsaturated and polymerizable, such as multi-basic acids or their reactive, readily hydrolyzing derivatives. Especially preferred multibasic acids are hydroxy acids such as tartaric or citric acid.

Compounds that have chelating groups but do not contain carboxylic acid groups or readily hydrolyzing acid-derivative groups are preferably included in composition in accordance with the invention, for example vanillates, syringates, and salicylates.

Mixing the compositions of the present invention may be achieved using standard compounding techniques. For example, liquids, photoinitiator(s), and accelerator(s) are blended first, and fillers are added incrementally thereafter. When blending light sensitive compositions, however, a photosafe room illumination, i.e., one that does not contain substantial amounts of wavelengths of electromagnetic radiation that would activate the photoinitiating system is used to avoid initiating polymerization of the composition prematurely.

Cements

The salt compounds of compositions of the present invention also have medical applications such as in self adhesive bone cements. However, they are most preferred to use in dental treatment by application to a tooth or a number of teeth in vivo, in the mouth of a live patient by a dentist or dental practitioner.

The application of the compositions of the invention is preferably as a dental cement applied to tooth. The dental cement compositions of the invention preferably include a salt compound within the scope of general formula I, and other ingredients, such as curing catalysts, initiators, accelerators, diluents and/or adjuvants. The composition is applied as a cement using conventional techniques and preferably cured with application of visible light in a conventional manner. Cements in accordance with the invention are self adhesive to dentin and enamel. These cements are used in bonding dentin to structures, for example, to bond a ceramic inlay to a prepared cavity of a tooth. Inlays preferably are polymers, or ceramics which are cast or built-up from porcelain frits and fired. Alternatively, inlays are machined from metal such as titanium or gold or preformed polymeric composite or homogeneous monolithic polymer compositions, for example by CAD-CAM procedures. In accordance with a preferred embodiment of the invention metal or ceramic superstructures for crowns, and bridges and/or orthodontic appliances are bonded to teeth using cement compositions of the invention. Such cement compositions join metal or ceramic to tooth by application of the cement composition by bringing them into contact until the cement hardens.

A preferred composition of the invention includes a two-part system. One part includes a curing agent. The two parts are spatuled to form a cement prior to placement on tooth. The placement is by standard technique(s). Preferably the cement includes a visible light and/or a self-curing redox polymerization initiator system. In a preferred embodiment of the invention luting cement compositions have low viscosity and film thicknesses less than about 25 μm to bond close fitting appliances to prepared teeth. In one embodiment luting cement compositions of the present invention may be prepared of such high viscosity and consistency that they form adhesive "glue" lines of thicknesses up to several hundred microns to lute less close fitting restorations, for example inlays prepared using present state-of-the-art CAD-CAM devices. Compositions of the invention are mechanically strong, abrasion resistant, and are esthetically suitable and serve as the sole structural element to retain inlay, crowns and bridges or other appliances to tooth structure.

Filling Compositions

A preferred dental treatment in accordance with the invention is the application of dental filling compositions which include a curing agent and at least one salt compound within the scope of general formula I. Preferably the dental filling composition includes finely divided reactive filler that can react ionically with the acids or acid derivatives of the monomer. Preferably the composition is applied to a tooth as a filling material using conventional techniques as a one-component material and is cured with application of visible light in conventional manner.

Pit and Fissure Sealants

In a preferred embodiment of the invention a one or two component pit and fissure sealant which includes at least one salt compound within the scope of general formula I is applied to anatomic defects and/or the exterior of teeth. The sealant limits the ability of caries-forming bacteria to colonize the pits, fissures and other surfaces of the teeth. Pit and fissure sealant compositions in accordance with the invention are an especially valuable means of reducing caries by filling and eliminating enamel defects. The pit and fissure sealants of the invention are preferably applied without prior acid etching or the use of rubber dam to teeth. In one embodiment fluoride eluting compounds and glasses are preferably included in compositions of the invention. Fluoride is eluted to reduce the incidence of caries in tooth substance adjacent the compositions of the invention.

In accordance with the method of the invention cement and restorative compositions include at least one polymerizable acid reactive ethylenically unsaturated compound within the scope of general formula I. Such compositions are applied to tooth without prior etching of the tooth.

*Method for Measurement of Compressive Strength Using International Standard Organization*(ISO) 9917:1991(E) at pages 5–7 Dental Water-based Cements For each material to be tested, cylinders 4 mm diameter and 6 mm long were prepared by filling the mixed material into teflon molds and light curing from each end for 40 seconds using The MAX Lite. The cylinders were removed from the molds and stored in water at 37° C. for 24 hours prior to testing. The force needed to load the specimens to breaking point was measured using a universal testing machine operating at a crosshead speed of 5 mm/min.

*Method of Transverse Flexural Strength Using International Standard Organization*(ISO)4049:1988(E) at pages 6–8 Resin-based Filling Materials The uncured material was filled into a split Teflon® mold with internal dimensions 25 mm×2 mm×2 mm. The exposed faces were then covered with polyester foil and clamped between transparent plastic blocks. The material was light cured for a total of 120 seconds by moving a dental curing light evenly backwards and forwards along the mold with the wand of the light in contact with the plastic blocks. After curing, the hardened specimens were stored in water at 37° C. for 24 hours. Before being tested, any remaining flash along the edges of the specimens was carefully removed and the exact dimensions of each specimen measured. The specimens were then tested in three point bending mode using a universal testing machine set to a crosshead speed of 0.75 mm/min, with the sample resting on supports 20 mm apart and being loaded at the mid point. The transverse bending strength was calculated from the standard formula in Megapascals (MPa).

Method for Measurement of Diametral Tensile Strength

Modified procedures of ADA Specification No. 9 and No. 27 were utilized for all materials tested. Split teflon molds with internal dimensions of 3 mm±0.1 mm high and 6 mm±0.1 mm diameter were used. Mylar film was placed at the bottom of the mold. After the mixed material was conveyed into the mold in excess, a second piece of mylar film was placed on top of the mold and pressed with a metal plate to squeeze out excess material. The plate was then removed with the mylar still in place on top of the material and each side was cured for one minute using The MAX Lite. After being stored in 37° C. water for 24 hours, specimens were tested on an Instron device for measurement of diametral tensile strength rising a 10 mm/minute crosshead speed.

Measurement of Adhesion to Dentin: Bond Strength to Dentin

Extracted human teeth used for the shear bond strength test was treated in 1% sodium hypochlorite for 18 to 24 hours and stored in distilled water in a refrigerator at about 4° C. until needed. The teeth were washed with water, mechanically sanded with 120/320/600 grit carborundum paper until a flat dentin surface was exposed.

The teeth were then individually prepared as follows. Each tooth was blown dry with compressed dry air to ensure the dentin surface was free from noticeable moisture. A small plastic straw with 3.7 mm inner diameter and 2 to 3 mm in length was filled with mixed material and seated on the dentin so as to form a post without pressure. The upper open end of the straw was covered with a thin film and cured with The MAX Lite for 40 seconds. The specimens were then stored in distilled water at 37° C. for more than 24 hours. The teeth were then vertically mounted in a one inch phenolic ring using self curing polymethyl methacrylate resin to provide a base for testing with the post at right angles thereto. The mounted specimens were loaded in shear in an Instron device for measurement of adhesion of the post to dentin at 5 mm/minute crosshead speed. The load was applied parallel to the prepared tooth surface and at right angles to the post until fracture occurred. The shear bond strength was calculated.

Method of Fluoride Release—Static Extraction

A 1 mm thick by 20 mm diameter chip of the material was cured for 1 minute on each side with the Max Lite. A tiny hole was drilled in the chip. The specimen was tied with a nylon thread, suspended in 10 ml deionized water in a plastic jar caped with a lid, and stored in 37° C. oven for one week, or otherwise indicated. Water in each jar was decanted to a separate 30 ml plastic beaker. The specimen in the jar was washed in 1 ml deionized water, and the water rinse was added to the respective beaker. To the jar, 10 ml of fresh deionized water was added and put back in the 37° C. oven for the next measurement. The solution was diluted with 11 ml Total Ionic Strength Adjustor Buffer (TISAB) solution and measured with fluoride electrodes.

This method is used to simulate what happens in the mouth over a long period of time. The water is changed weekly. The values are reported in ppm, in micrograms of fluoride per gram of sample, and in micrograms of fluoride per centimeter square of sample surface.

Having generally described the invention, a more complete understanding can be obtained with reference to certain specific examples, which are included for purposes of illustration only. It should be understood that the invention is not limited to the specific details of the Examples.

EXAMPLE 1

6FDMA is the reaction product of 1 mole of hexafluoroisopropylidine-2,2 bis(phthalic acid anhydride) and 2 moles of 2-hydroxyethyl methacrylate, identified hereafter as HEMA.

13.3 grams (0.03 moles) hexafluoroisopropylidine-2,2bis (phthalic acid anhydride) and 12.6 grams (0.097 moles) of HEMA and 0.0006 grams of butylated hydroxytoluene are heated in a 100 ml round bottom flask equipped with a thermometer and a water cooled condenser with a drying tube. The mixture is stirred while heating slowly to 100° C. Thereafter the temperature is maintained at 110° C. for one hour, then 16 hours overnight at 50° C., then a further 3.5 hours at 110° C. The solution is cooled to room temperature. The solution contains 70% by weight of 6FDMA and 30% by weight of HEMA and has IR absorptions at: 2500–3500 $cm^{-1}$, broad; 1715 $cm^{-1}$ broad; 1630 $cm^{-1}$; 1130–1450 $cm^{-1}$ broad; 1170 $cm^{-1}$; 950 $cm^{-1}$; and 800 $cm^{-1}$ multiplet.

EXAMPLE 2

Synthesis of BTDMA

BTDMA is the reaction product of 1 mole of 3,3',4,4'-benzophenone tetracarboxylic acid dianhydride and 2 moles 2-hydroxyethyl methacrylate. When prepared in an excess of 2-hydroxyethyl methacrylate the HEMA serves as a solvent for the esterification reaction.

50 grams (0.155 moles) 3,3',4,4'-benzophenone tetracarboxylic acid dianhydride (Aldrich Chem) is reacted with 82.7 grams HEMA (0.635 moles) (Aldrich Chemical) at 120° C. for 1 hour to provide a clear thick liquid containing BTDMA in an excess HEMA, having IR absorptions at 3000 to 3550 $cm^{-1}$, very broad; 2950 $cm^{-1}$ broad; 1720 $cm^{-1}$, broad; 1630 $cm^{-1}$; 1370–1450 $cm^{-1}$ multiplets; 1100–1340 $cm^{-1}$ very broad; 1160 $cm^{-1}$; 940 $cm^{-1}$; 810 $cm^{-1}$; and 650 $cm^{-1}$. This solution contains 70% by weight of BTDMA and 30% of HEMA.

EXAMPLE 3

Synthesis of OEMA

OEMA is the reaction product of 1 mole 4,4'oxydiphthalic anhydride (chemical name: 5,5'-oxybis-1,3-isobenzo furandione) and 2 moles of HEMA.

35.6 grams (0.115 moles) of 4,4'-oxydiphthalic anhydride and 58.0 grams (0.045 moles) of HEMA are reacted at 110° C. for 4 hours to provide a clear oily solution of OEMA in an excess of HEMA, having a viscosity of 5250 cps, and IR absorptions at 2700–3550 $cm^{-1}$ very broad; 1715 $cm^{-1}$ broad; 1630 $cm^{-1}$, 1590 $cm^{-1}$; 1570 $cm^{-1}$; 1450 $cm^{-1}$; 1400 $cm^{-1}$; 1360 $cm^{-1}$; 1100–1330 $cm^{-1}$; 1165 $cm^{-1}$; 940 $cm^{-1}$; 810 $cm^{-1}$, and 785 $cm^{-1}$. This solution contains 70% by weight OEMA and 30% by weight of HEMA.

EXAMPLE 4

Synthesis of OPMA

OPMA is the reaction product of 1 mole oxydiphthalic anhydride and 2 moles of HPMA.

18.0 grams (0.058 moles) of 4,4'oxydiphthalic anhydride (Occidental Petroleum) and 32.6 grams (0.226 moles) hydroxypropyl methacrylate HPMA (Aldrich) are reacted at 110° C. while stirring for 3 hours at 110° C. to provide a clear oily solution of OPMA in an excess of HPMA having a viscosity after reaction of 3250 cps at 23° C. and the OPMA having IR absorptions at 3100–3550 cm$^{-1}$ very broad; 2900–3000 cm$^{-1}$; 1715 cm$^{-1}$; 1630 cm$^{-1}$; 1590 cm$^{-1}$; 1570 cm$^{-1}$; 1445 cm$^{-1}$; 1400 cm$^{-1}$; 1100–1330 cm$^{-1}$; 1060 cm$^{-1}$; 940 cm$^{-1}$; 810 cm$^{-1}$. This solution contains 70% by weight OPDMA and 30% by weight of HEMA.

EXAMPLE 5
Preparation of STDMA

STDMA is the reaction product of 1 mole of 4,4'-sulfonyldiphthalic dianhydride (STDA) and 2 moles of HEMA. In this example STDMA is prepared in an excess of HEMA.

26.9 grams (0.207 moles) HEMA, 10.4 grams (0.029 moles) STDA and 0.044 grams BHT are placed in a 100 ml flask and heated to 90° C. The mixture is held for 1.5 hours at 90° C. to 95° C. and 1.33 hours at 115° C. to 120° C. Then 0.11 grams triphenyl phosphine, 10.2 grams (0.028 moles) STDA, and 4.3 grams (0.033 moles) HEMA are added to the mixture and held at 115° C. to 120° C. for an additional 1.5 hour to form a solution containing 68.6% by weight of STDMA and 31.4% by weight of HEMA having IR absorptions at 3500 cm$^{-1}$, very broad; 1715 cm$^{-1}$ 1635 cm$^{-1}$; 1300 cm$^{-1}$ broad, and 1150 cm$^{-1}$ broad. This solution contains 68.6% by weight of STDMA and 31.4% by weight of HEMA.

EXAMPLE 6
Preparation of OEMA in TEGMA

OEMA is the reaction product of 1 mole of oxydiphthalic dianhydride (ODPA) and 2 moles of HEMA.

In this example product is prepared in triethylene glycol dimethacrylate (TEGDMA) as a solvent.

19.6 grams (0.063 moles) of ODPA, 30 grams (0.23 moles) HEMA, 0.046 grams of monomethyl hydroquinone and 20 grams of TEGDMA as a solvent are placed in a 250 ml flask. The mixture is heated with stirring to 95° C. to 100° C., and 0.06 grams of triphenyl phosphine as catalyst is added and held at 100° C. for an additional 25 minutes. Following this 15.5 grams (0.05 moles) of ODPA and 0.03 grams of triphenyl phosphine are added at 110° C. After stirring at 110° C. for 1.5 hours, 0.02 grams of triphenyl phosphine is added and held for one hour at 110° C. and then held at 50° C. for 7 days. At the end of that time all anhydride is consumed. The reaction forms a solution containing 76.5% by weight OEMA and 23.5% TEGMA. The OEMA which has IR absorptions at 2500 to 3550 cm$^{-1}$ very broad; 1700 cm$^{-1}$ broad; 1630 cm$^{-1}$, 1100–1450 cm$^{-1}$ very broad; 1050 cm$^{-1}$; 950 cm$^{-1}$; and 780–900 cm$^{-1}$. This solution contains 76.5% by weight of OEMA and 23.5% by weight of TEGMA.

Preparation of Powders

Strontium aluminofluorosilicate glass powder used in Examples 12, 13 and 17 is made by fusing aluminum oxide, silica, strontium fluoride, aluminum fluoride, aluminum phosphate, and cryolite according to procedures disclosed in U.S. Pat. No. 4,814,362 to form particles which are milled to a mean particle size of 5.5 microns. It has the following analysis with all elements except fluorine being calculated as the oxide of the element:

| aluminofluorosilicate glass particles | Parts by weight |
| --- | --- |
| $Al_2O_3$ | 24.6 |
| $SiO_2$ | 32.1 |
| $Na_2O$ | 2.9 |
| SrO | 28.7 |
| F | 12.3 |
| $P_2O_5$ | 4.8 |

The barium aluminofluorosilicate glass particles used in Examples 8, 10 and 12 through 16 are 7726 glass sold by Corning. It is preferably formed as disclosed in Danielson U.S. Pat. No. 4,920,082.

EXAMPLE 7
Synthesis of OEMA/GMA Resin 31.0 grams (0.1 mole) 4,4-oxydiphthalic anhydride (ODPA), 11.4 grams of glutaric anhydride (0.1 mole), 39.0 grams of hydroxyethyl methacrylate (HEMA), (0.30 mole), and 0.05 grams of butylated hydroxytoluene are reacted at room temperature for 30 minutes followed by stirring at 110° C. for 2.0 hours to form a very viscous mixture of the adduct of ODPA and HEMA (OEMA) and an adduct of glutaric anhydride and HEMA (GMA).

EXAMPLE 8
One Component VLC Composition 30.50 grams of OEMA/GMA resin are formed as described in Example 7; 2.50 grams of water; 65.10 grams of 2,7,7,9,15-pentamethyl-4,13-dioxo-3,14-dioxa-5,12-diaza-hexadecane-1,16-diyl dimethacrylate (UDMA); 0.20 grams of camphorquinone; 0.60 grams of EDAB; 1.00 gram of 2-hydroxy-4-methoxybenzophenone (Uvinol M-40 sold by BASF) and 0.50 grams of butylated hydroxytoluene (BHT) are stirred to form an activated resin. 5.0 grams of the activated resin is mixed with 15.0 grams of barium aluminofluorosilicate glass powder (67% silanated and 33% unsilanated) to form a paste having a shelf stable polymerizable complex which does not set within 6 months in the absence of polymerization initiation. The paste is cured by transmission thereinto of visible light from The Max lite™ polymerization unit sold by Dentsply International Inc to form a polymeric material having a compressive strength of 31533 psi.

EXAMPLE 9
Synthesis of 6-FDMA/PMA Resin Adducts with HEMA 39.0 grams of HEMA, 0.06 g butylate hydroxytoluene, and 14.8 grams of phthalic anhydride are reacted at 100–110° C. for 60 minutes. Then 44.4 grams of hexafluoroisopropylidene-2,2-bis (phthalic acid anhydride) is added and stirred at between 120° and 130° C. for 4.0 hours to form a clear, slightly yellow resin, mixture of 6FDMA and an adduct of phthalic anhydride and HEMA (PMA).

EXAMPLE 10
One Component VLC Composition 30.10 grams of 6-FDMA/PMA resin formed by following the procedure of Example 9; 2.50 grams of water; 65.10 grams of UDMA; 0.20 grams of camphorquinone; 0.60 grams of EDAB; 1.00 gram of 2-hydroxy-4-methoxybenzophenone (Uvinol M-40); and 0.50 grams of butylated hydroxytoluene are stirred to form an activated resin. 2.50 grams of the activated resin is mixed with 75.0 grams barium aluminofluorosilicate glass (60% silanted 40% unsilanated) to form a paste having a shelf stable polymerizable complex. The paste is cured by transmission thereinto of visible light from a The Max lite™ polymerization unit sold by Dentsply International Inc to form polymeric material having a compressive strength of 29334 psi; a flexural strength of 72.1 MPA and a flexural modulus of 8939.6 MPA.

EXAMPLE 11
Synthesis of 6-FDMA/GMA Resin 39.0 grams (0.30 mole) hydroxyethylmethacrylate, 44.4 grams of hexafluoroisopropylidene-2,2-bis (phthalic acid anhydride), 12.0 grams of glutaric anhydride and 0.06 grams of butylated hydroxytoluene are reacted at 100° C. for 4.0 hours to form a viscous slightly yellow clean resin, mixture of 6-FDMA and an adduct of glutaric anhydride and HEMA (GMA).

EXAMPLE 12

A one component VLC paste composition is formed by mixing 9.20 grams of 6-FDMA/GMA(formed by following the procedures of Example 11), 0.80 grams of water; 15.0 grams of urethane dimethacrylate (2,7,7,9,15-pentamethy-4,13-dioxo-3,14-dioxa-5,12-diaza-hexadecane-1,16-diyl dimethacrylate); 0.05 grams of camphorquinone; 0.30 grams of ethyl-4-dimethylaminobenzoate (EDAB); 0.0125 grams of butylated hydroxytoluene; 0.075 grams of Uvinol M-40; 37.5 silanated strontium aluminofluorosilicate glass powder and 37.5 grams of silanated barium aluminofluorosilicate glass. The paste is cured by transmission thereinto of visible light from The Max lite™ polymerization unit sold by Dentsply International Inc to form polymeric material having a flexural strength of 82 MPa; a flexural modulus of 10948; and compressive strength of 31954 psi.

EXAMPLE 13

10.75 grams of adduct of hexafluoroisopropylidene-2,2-bis (phthalic anhydride) and 2-hydroxyethyl methacrylate, 4.61 grams of 2-hydroxyethyl methacrylate, 7.2 grams of triethylene glycol dimethacrylate, and 0.98 grams of water are mixed with 0.048 grams of bicyclo (2,2,1) heptane-2,3-dione 1,7,7-trimethyl, 0.144 grams of 4-ethyl dimethylaminobenzoate, 0.24 grams of methanone (2-Hydroxy-methoxyphenyl) phenyl, and 0.024 grams of 2,6-bis(1,1-dimethethyl)-4-methyl phenol to form a polymerizable liquid. 37.24 grams of silanated strontium aluminofluorosilicate, 38.0 grams of barium aluminofluorosilicate glass, 0.76 grams of aerosil R-972 are formed into a power blend which is then mixed with the polymerizable liquid to form a one-component light curable dental adhesive paste composition which does not set within 6 months of polymerization initiation. The paste is cured by transmission thereinto of visible light from a The Max lite™ polymerization unit sold by Dentsply International Inc to form polymeric material having the properties shown in Tables 1 and 2.

TABLE 1

COMPARISON OF PHYSICAL PROPERTIES

| PROPERTY | STANDARD ISO 9917 | STANDARD ISO 4049 | SELF ADHESIVE COMPOSITE OF EXAMPLE 13 |
| --- | --- | --- | --- |
| COMPRESSIVE STRENGTH (MPa) | >130 | | 234 |
| FLEXURAL STRENGTH (MPa) | | >50 | 69 |
| FLEXURAL MODULUS (MPa) | | | 7953 |
| DIAMETRAL STRENGTH (MPa) | | | 43 |
| OPACITY Co. 70 | >0.35 <0.90 | | >0.35, <0.55 |
| RADIOPACITY mm Al | | >1 mm Al | 3 mm |
| COLOR STABILITY | | SLIGHT CHANGE | PASS |
| SENSITIVE TO AMBIENT LIGHT | | NO CHANGE IN 1 MINUTE | PASS |
| DEPTH OF CURE (mm) | | >2 | 3 4.5 |
| ADHESION TO DENTIN (MPa) unetched | | | 5 |
| ADHESION TO ENAMEL (MPa) unetched | | | 5 |
| ACID SOLUBLE: | | | |
| Pb content mg/kg | <100 | | <2 |
| Rs content mg/kg | <2 | | <1 |
| % SALT FORMED BY TITRATION AFTER 2 MONTHS STORAGE AT 70° F. TEMPERATURE | | | 20.8 |

TABLE 2

STATIC FLUORIDE RELEASE

| $\mu$g/gram of sample | Cum. $\mu$g/gram of sample |
| --- | --- |
| 142.54 | 142.54 |
| 111.83 | 254.37 |
| 95.16 | 349.54 |
| 91.15 | 440.68 |
| 72.30 | 512.99 |
| 73.69 | 586.67 |
| 59.59 | 646.26 |
| 62.68 | 708.94 |

Sample used to prepare Table 2 had an average weight grams of 0.678, an average diameter cm of 2.039, and average thickness cm of 0.094 and an average surface area of 7.13.

EXAMPLE 14

A one component VLC composition is formed by stirring 10.75 grams of 6-FDMA (formed by following the procedure of Example 1), 4.61 grams of HEMA, 7.2 grams of TEGDMA, 0.98 grams of distilled water, 0.048 grams of camphorquinone, 0.144 grams of EDAB, 0.24 grams of Uvinol M-40 and 0.024 grams of BHT at room temperature to form a homogeneous activated resin. 2.4 grams of the activated resin is mixed with 7.6 grams of a powder blend of 99 grams of barium aluminofluorosilicate glass, 1 gram of Aerosil R-972 to make a stable paste. The paste is cured to form a polymeric adhesive having a compressive strength of 225 MPa, a bond strength to dentin of 1673 psi and a fluoride release shown in Table 3.

EXAMPLE 15

One component VLC sealant is formed by mixing 25.24 grams of OEMA, (formed by following the procedure of Example 3) 12.5 grams TEGDMA, 2.0 grams of distilled water, 0.04 grams of camphorquinone, 0.2 grams EDAB and 0.016 grams BHT to an homogeneous activated resin. 40 grams of barium aluminofluorosilicate glass is added to the resin to form a stable one component VLC sealant having which upon exposure to visible light forms a polymeric material having a compressive strength of 25521 psi, flexural strength 42 MPa, flexural modulus of 4071 MP and releases fluoride as shown in Table 3.

EXAMPLE 16

One component VLC sealant is formed by stirring 30.93 grams 6-FDMA formed by following the procedure of Example 1, 1.93 grams distilled water, 14.98 grams TEGDMA, 0.05 grams of camphorquinone, 0.24 grams EDAB and 0.025 grams BHT to form an activated resin, then add 51 grams barium aluminofluorosilicate glass and 0.77 grams aerosil R-972. The mixture is mixed to form a stable one component sealant which upon curing by exposure to visible light forms a polymeric material having a compressive strength of 31552 psi, dimetrial tensile strength of 5085 psi, flexural strength 74 MPa, flexural modulus of 3722 MPa., and a bond strength to enamel of 1160 psi.

The static fluoride release for samples of products from Examples 14, 15, and 16 are shown in Table 3.

TABLE 3

STATIC RELEASE OF FLUORIDE IN MICROGRAMS OF FLUORIDE PER GRAM OF SAMPLE

| Week | Polymeric Product of Example 14 | Polymeric Product of Example 15 | Polymeric Product of Example 16 |
| --- | --- | --- | --- |
| 1  | 857.5 | 509.6 | 479.4 |
| 2  | 720.3 | 296.3 | 433.0 |
| 3  | 545.3 | 296.3 | 376.9 |
| 4  | 458.6 | 374.2 | 327.4 |
| 6  | 373.3 | 283.6 | 311.9 |
| 7  | 337.4 | 299.6 | 279.5 |
| 8  | 282.9 | 265.4 | 146.1 |
| 9  | 268.7 | 261.8 | 146.1 |
| 10 | 239.7 | 247.3 | 146.1 |
| 11 |       | 232.0 | 226.8 |
| 12 |       | 200.8 | 201.2 |

Polymerizable Salt Formation 1.0 grams $Ca(OH)_2$, and a solution of 0.95 grams 6FDMA, 0.27 grams HEMA and 0.08 grams water are mixed. The IR spectrum of the mixture is measured immediately and shows neutralization of the acid and a broad IR absorption at 1390 $cm^{-1}$ and 1580 $cm^{-1}$, indicating formation.

1.0 grams of $Al_2O_3$, a solution of 0.65 grams 6FDMA, 0.27 grams and 0.08 grams of water are mixed. The IR spectrum of the mixture indicates salt formation by absorption at 1390 $cm^{-1}$ and 1580 $cm^{-1}$.

EXAMPLE 17

A resin mixture of 6 grams of an adduct of succinic anhydride and glycerol dimethacrylate (SGMA), 1.2 grams of dipentaeryothritol pentaacrylate phosphate (DPEPAP), prepared as described in U.S. Pat. No. 4,514,342, 2.4 grams of 2,2-bis [4-(2-hydroxy-3-methacryloxypropoxy)phenyl], (Bis-GMA), 0.573 grams of water, 0.02 grams of camphorquinone, 0.049 grams of EDAB and 0.01 grams of butylated hydroxytoluene (BHT) is mixed in a 50 ml plastic beaker to form a homogeneous liquid. Then, 31 grams of strontium aluminofluorosilicate glass powder is added and mixed to form a uniform paste. The paste is cured by transmission thereinto of visible light from a The Max lite™ polymerization unit sold by Dentsply International Inc to form a polymeric material having static fluoride release shown in Table 4.

TABLE 4

| WEEKS | ppm | μg | μg/gram | Cum · μg/gram |
| --- | --- | --- | --- | --- |
| 1  | 7.5400 | 82.94 | 93.37 | 93.37 |
| 2  | 4.0050 | 44.06 | 49.59 | 142.96 |
| 3  | 3.4850 | 38.34 | 43.16 | 186.12 |
| 4  | 2.7900 | 30.69 | 84.44 | 220.67 |
| 5  | 2.2700 | 24.97 | 28.11 | 248.78 |
| 6  | 2.0800 | 22.88 | 25.76 | 274.54 |
| 7  | 1.9300 | 21.23 | 23.90 | 298.44 |
| 8  | 1.9150 | 21.07 | 23.71 | 322.15 |
| 9  | 1.6450 | 18.10 | 20.37 | 342.52 |
| 10 | 1.1450 | 12.60 | 14.18 | 356.70 |
| 11 | 1.2500 | 13.75 | 15.48 | 372.18 |
| 12 | 1.1480 | 12.53 | 14.22 | 386.39 |
| 13 | 1.0325 | 11.36 | 12.79 | 399.18 |
| 14 | 1.0325 | 11.36 | 12.79 | 411.96 |

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A one component polymerizable pliable paste product formed by a process comprising:

forming a polymerizable pliable paste composition comprising water and a polymerizable material within the scope of the general formula:

$$\left[\left[(\text{Group})_o\,(\text{Divalent})_s\,(A)_{\overline{p}}\right]_r(M)\right]_t\!\!-\!\!\text{Particle}$$

wherein each Group independently is an addition polymerizable group, each A independently is a carboxylic, organic sulfur containing or phosphorus-containing acid group, each Divalent independently is a divalent organic moiety, and each M independently is a multivalent cation of Particle and forms a complex by bonding to one or more A, said Particle having a size between 0.02 and 50 microns, r, t, o, p and s each independently is a number having an average value of 1 or more, and storing said polymerizable pliable paste composition for at least 24 hours without substantial setting to provide a one component polymerizable pliable paste product.

2. The composition of claim 1 wherein said M is barium, calcium, strontium or aluminum.

3. The composition of claim 1 wherein A is a carboxylic moiety.

4. The composition of claim 1 further comprising acrylic monomer, and said acrylic Monomer and said complex each independently comprises at least 1 percent by weight of said composition.

5. The composition of claim 1 wherein said complex comprises at least 3 percent by weight of said composition.

6. The composition of claim 1 wherein Particle comprises glass with a particle size having a longest dimension less than 0.1 mm and further comprising a polymerization initiator.

7. The composition of claim 1 wherein said complex is within general formula $$\left[R_1\!\!-\!\!\underset{Z_1}{\underset{|}{\bigcirc\!\!\bigcirc}}\!\!\right]_n\!\!\overset{X}{\diagdown}\!\!\left[\underset{Z_2}{\underset{|}{\bigcirc\!\!\bigcirc}}\!\!-\!\!R_2\right]_m\!\!-\!\!M\Bigg]_l$$

wherein X is $$O,\ S,\ \underset{O}{\overset{O}{\overset{\|}{S}}},\ \underset{O}{\overset{O}{\overset{\|}{S}}},\ \underset{|}{\overset{R_9}{\overset{|}{N}}},\ \underset{R_{11}}{\overset{R_{10}}{\overset{|}{P}}},\ \underset{OR_{12}}{\overset{OR_{13}}{\overset{|}{P}}},\ \underset{|}{\overset{O}{\overset{\|}{P}}},\ \underset{OR_{14}}{\overset{O}{\overset{\|}{P}}},\ O\!\!-\!\!\underset{OR_{14}}{\overset{O}{\overset{\|}{P}}}\!\!-\!\!O,$$

$$-\!\!\underset{R_4}{\overset{R_3}{\overset{|}{C}}}\!\!-,\quad\text{or}\quad (O)_a\!\!-\!\!\left[\underset{R_6}{\overset{R_5}{\overset{|}{(C)}}}_b\!\!-\!\!O\right]_p\!\!-$$

$R_1$ and $R_2$ each independently is a polymerizable unsaturated moiety having from 2 to 13 carbon atoms, $R_3$, $R_4$, $R_5$, and $R_6$ each independently is hydrogen, halogen, alkyl of from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $Z_1$ and $Z_2$ each independently is a moiety including an acid group or a reactive acid derivative, a, m and n each independently is 0 or 1, b, and p each independently is an integer from 1 to 10; and l is a integer from 1 to 3 and M is multivalent cation.

8. The composition of claim 7 in the composition further comprising a diluent comonomer.

9. The composition of claim 7 in a composition further comprises glass particles.

10. The composition of claim 7 wherein n and m are zero.

11. A one component polymerizable pliable paste product formed by a process, comprising: forming a polymerizable pliable paste composition comprising water and a polymerizable material within the scope of the general formula:

$$\left[\left[(\text{Group})_o\,(\text{Divalent})_s\,(A)_{\overline{p}}\right]_r(M)\right]_t\!\!-\!\!\text{Particle}$$

wherein each Group independently is an addition polymerizable group, each A independently is a carboxylic, organic sulfur containing or phosphorus-containing acid group, each Divalent independently is a divalent organic moiety, and each M independently is a multivalent cation of glass Particle and forms a complex by bonding to one or more A, r, t, o, p and s each independently is a number having an average value of 1 or more, and storing said composition for at least 24 hours without substantial setting to provide a one component polymerizable pliable paste product.

12. The composition of claim 11 wherein said M is barium, calcium, strontium or aluminum.

13. The composition of claim 11 wherein A is a carboxylic moiety and Y is alkylene.

14. The composition of claim 11 further comprising acrylic monomer, and said acrylic Monomer and said complex each independently comprises at least 1 percent by weight of said composition.

15. The composition of claim 11 wherein said complex comprises at least 3 percent by weight of said composition.

16. The composition of claim 11 wherein Particle comprises glass with a particle size having a longest dimension less than 0.1 mm and further comprising a polymerization initiator.

17. The composition of claim 11 wherein said complex is within general formula $$\left[R_1\!\!-\!\!\underset{Z_1}{\underset{|}{\bigcirc\!\!\bigcirc}}\!\!\right]_n\!\!\overset{X}{\diagdown}\!\!\left[\underset{Z_2}{\underset{|}{\bigcirc\!\!\bigcirc}}\!\!-\!\!R_2\right]_m\!\!-\!\!M\Bigg]_l$$

wherein X is $$O,\ S,\ \underset{O}{\overset{O}{\overset{\|}{S}}},\ \underset{O}{\overset{O}{\overset{\|}{S}}},\ \underset{|}{\overset{R_9}{\overset{|}{N}}},\ \underset{R_{11}}{\overset{R_{10}}{\overset{|}{P}}},\ \underset{OR_{12}}{\overset{OR_{13}}{\overset{|}{P}}},\ \underset{|}{\overset{O}{\overset{\|}{P}}},\ \underset{OR_{14}}{\overset{O}{\overset{\|}{P}}},\ O\!\!-\!\!\underset{OR_{14}}{\overset{O}{\overset{\|}{P}}}\!\!-\!\!O,$$

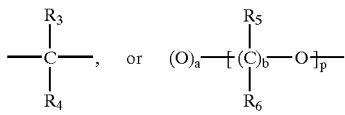

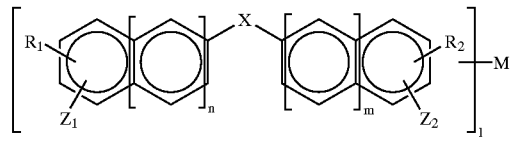

$R_1$ and $R_2$ each independently is a polymerizable unsaturated moiety having from 2 to 13 carbon atoms, $R_3$, $R_4$, $R_5$, and $R_6$ each independently is hydrogen, halogen, alkyl of from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $Z_1$ and $Z_2$ each independently is a moiety including an acid group or a reactive acid derivative, a, m and n each independently is 0 or 1, b, and p each independently is an integer from 1 to 10; and l is a integer from 1 to 3 and M is multivalent cation.

18. The composition of claim 17 in the composition further comprising a diluent comonomer.

19. The composition of claim 17 in a composition further comprises glass particles.

20. The composition of claim 17 wherein n and m are zero.

21. The composition of claim 11 in a composition further comprising a source of fluoride ion.

22. A method of adhering a one component pliable paste dental cement product to tooth, comprising:

providing a one component pliable paste dental cement product formed by a process comprising, providing a polymerizable composition, comprising: water and a polymerizable material within the scope of the general formula:

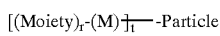

wherein each Moiety independently is a moiety having at least one carboxylic, organic sulfur containing or phosphorous containing acid group and at least one addition polymerizable group, each M is a multivalent cation of glass Particle and forms a complex by bonding to one or more Moiety, r is a number having an average value of 1 or more, and storing said composition for at least 24 hours in the absence of polymerization initiation to form a one component pliable paste dental cement product, and applying said one component pliable paste dental cement product to tooth.

23. The method of claim 22 wherein said applying is without prior treatment of said tooth material, except cleaning to increase adhesion of said cement to said tooth.

24. The method of claim 22 wherein M is barium, calcium, aluminum or strontium.

25. The method of claim 22 further comprising a diluent comonomer.

26. The method of claim 22 wherein said complex is within general formula:

wherein X is

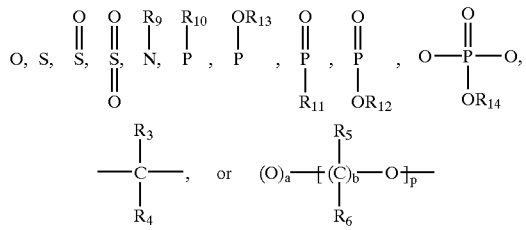

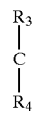

$R_1$ and $R_2$ each independently is a polymerizable unsaturated moiety having from 2 to 13 carbon atoms, $R_3$, $R_4$, $R_5$, and $R_6$ each independently is hydrogen, halogen, alkyl of from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $Z_1$ and $Z_2$ each independently is a moiety including an acid group or a reactive acid derivative, a, m and n each independently is 0 or 1, b, and p each independently is an integer from 1 to 10; 1 is an interger from 1 to 3 and M is multivalent cation.

27. The method of claim 26 wherein n and m are zero.

28. The method of claim 26 wherein X is oxygen or $$\begin{array}{c} R_3 \\ | \\ C \\ | \\ R_4 \end{array}$$

wherein $R_3$ and $R_4$ are fluorinated methyl moieties.

29. A method of using a dental product consisting essentially of:

providing a one component pliable polymerizable paste dental composition comprising: water and- a polymerizable material within the scope of the general formula:

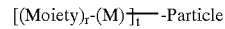

wherein each Moiety independently is a moiety having at least one carboxylic, organic sulfur containing or phosphorous containing acid group and at least one addition polymerizable group, each M is a multivalent cation of glass Particle and forms a complex by bonding to one or more Moiety, and t and r each independently is a number greater than or equal to 1, and storing said pliable polymerizable paste dental composition for at least 24 hours in the absence of polymerization initiation to form a pliable polymerizable paste dental product, and applying said pliable polymerizable paste dental product to tooth and then polymerizing said polymerizable material to form a polymerized polymeric product.

30. The method of claim 29 wherein said polymerized product is a dental filling material, pit and fissure sealant, luting cement, base or orthodontic cement.

31. A method of polymerization, comprising the following sequence of steps:
  a) providing a one component substantially pliable polymerizable paste product formed by a process comprising providing an initial composition comprising: water, Particle and a polymerizable salt, setting said composition to form a substantially pliable polymerizable aqueous paste having a substantial portion of a complex within the scope of the general formula:

(Moiety)$_r$-(M)-Particle wherein each Moiety independently is a moiety having at least one carboxylic, organic sulfur containing or phosphorous containing acid group and at least one addition polymerizable group,
  each M is a multivalent cation of Particle and each M forms a complex by bonding to one or more Moiety, and
  r is a number having an average value of 1 or more, and
  storing said substantially pliable polymerizable paste composition for at least 12 hours to form a substantially pliable polymerizable paste product, and,
  b) applying said substantially pliable polymerizable paste product to a tooth.

32. A method of polymerization, comprising the following sequence of steps:
  a) providing a one component substantially pliable polymerizable paste product formed by a process, comprising: providing a one component substantially pliable polymerizable composition comprising water and a polymerizable complex within the scope of the general formula:

(Moiety)$_r$-(M)-Particle wherein each Moiety independently is a moiety having at least one carboxylic, organic sulfur containing or phosphorous containing acid group and at least one addition polymerizable group,
  each M is a multivalent cation of glass Particle and each M forms a complex by bonding to one or more Moiety, and
  r is a number having an average value of 1 or more,
  b) storing said pliable polymerizable paste composition for at least 12 hours to form a pliable polymerizable paste product, and
  c) applying said pliable polymerizable paste product to a tooth, and
  d) polymerizing said polymerizable complex in said pliable polymerizable paste product to form polymeric material.

33. The method of claim 32 wherein said polymeric material is a dental luting cement, liner, base or restorative.

34. A method of polymerization, comprising the following sequence of steps:
  a) providing a one component substantially pliable polymerizable paste product, formed by a process comprising: providing a one component substantially pliable polymerizable composition comprising water and a polymerizable complex within the scope of the general formula:

(Moiety)$_r$-(M)-Particle wherein each Moiety independently is a moiety having at least one carboxylic, organic sulfur containing or phosphorous containing acid group and at least one addition polymerizable group,
  each M is a multivalent cation of glass Particle and each M forms a complex by bonding to one or more Moiety, and
  r is a number having an average value of 1 or more,
  b) storing said polymerizable composition for at least 12 hours to form a one component substantially pliable polymerizable product, and
  c) applying said polymerizable product to a tooth, and polymerizing said polymerizable complex to form a polymeric coating on an outer surface of said Particle.

35. The method of claim 34 wherein said particle comprises glass with a longest dimension less than 0.1 mm.

36. The method of claim 34 wherein said particle comprises ionomeric polymer with a longest dimension less than 0.1 mm.

37. The method of claim 34 wherein said complex is within general formula $$\left[ R_1 \underset{Z_1}{\bigcirc\bigcirc}{}_n - X - \underset{Z_2}{\bigcirc\bigcirc}{}_m R_2 \right]_I - M$$

wherein X is $$O,\ S,\ \underset{\underset{O}{\|}}{\overset{O}{\|}}{S},\ \overset{O}{\|}{S},\ \underset{R_{11}}{\overset{R_9}{|}}{N},\ \underset{R_{11}}{\overset{R_{10}}{\overset{|}{P}}},\ \underset{OR_{12}}{\overset{OR_{13}}{\overset{|}{P}}},\ \underset{|}{\overset{O}{\|}}{P},\ \underset{OR_{12}}{\overset{O}{\|}}{P},\ \underset{OR_{14}}{O-\overset{O}{\overset{\|}{P}}-O},$$

$$-\underset{R_4}{\overset{R_3}{\overset{|}{C}}}-,\quad \text{or}\quad (O)_a-\left[\underset{R_6}{\overset{R_5}{\overset{|}{(C)}}}_b - O\right]_p -$$

$R_1$ and $R_2$ each independently is a polymerizable unsaturated moiety having from 2 to 13 carbon atoms,
$R_3$, $R_4$, $R_5$, and $R_6$ each independently is hydrogen, halogen, alkyl of from 1 to 10 carbon atoms or halogenated alkyl of from 1 to 10 carbon atoms,
$R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms,
$Z_1$ and $Z_2$ each independently is a moiety including an acid group or a reactive acid derivative, a, m and n each independently is 0 or 1, b, and p each independently is an integer from 1 to 10; and
I is a integer from 1 to 3 and M is multivalent cation.

38. A polymerizable one component pliable paste product formed by a process, comprising: providing a polymerizable one component pliable paste composition comprising water and a polymerizable material, said polymerizable material comprising:
  a compound having an addition polymerizable group,
  a carboxylic, organic sulfur containing or phosphorus-containing acid group and a divalent organic moiety, said compound being bonded to a multivalent cation of a glass particle,
  storing said composition for at least 24 hours effectively without setting to form an aqueous polymerizable paste product.

39. The product of claim 38 wherein said compound has a molecular weight less than 100,000.

* * * * *